United States Patent [19]

Bourzat et al.

[11] Patent Number: 5,223,529
[45] Date of Patent: Jun. 29, 1993

[54] N-PHENYLAMIDES AND MEDICINAL PRODUCTS CONTAINING THEM

[75] Inventors: Jean-Dominique Bourzat, Vincennes; Marc Capet, Bourg la Reine; Claude Cotrel, Paris; Claude Guyon, Mouthe; Gerard Roussel, Soisy sur Seine; Franco Manfre, Vitry sur Seine, all of France

[73] Assignee: Rhone-Poulenc Sante, France

[21] Appl. No.: 522,137

[22] Filed: May 11, 1990

[30] Foreign Application Priority Data

May 12, 1989 [FR] France ............... 89 06250

[51] Int. Cl.$^5$ ................. A01N 43/38; C07C 273/00; C07D 207/00
[52] U.S. Cl. .................. 514/414; 514/419; 514/423; 514/510; 514/513; 514/522; 514/535; 514/562; 514/563; 514/616; 548/537; 548/540; 548/467; 558/414; 558/415; 560/9; 560/21; 560/34; 560/47; 560/48; 567/427; 567/428; 567/434; 567/435; 567/437; 564/49; 564/50; 564/52; 564/53; 564/153; 564/154; 564/155; 564/158
[58] Field of Search .............. 564/49, 50, 52, 53, 564/155, 153, 154, 158; 548/538, 540, 537, 467, 491, 492; 558/414, 415; 560/9, 21, 34, 47, 48, 64, 65, 73; 562/427, 428, 435, 437, 439

[56] References Cited

U.S. PATENT DOCUMENTS

| | | | |
|---|---|---|---|
| 4,187,216 | 2/1980 | Hasall et al. | 548/538 |
| 4,303,673 | 12/1981 | Biedermann et al. | 564/155 |
| 4,410,697 | 10/1983 | Török et al. | 564/49 |
| 4,418,209 | 11/1983 | Douglas et al. | 509/49 |
| 4,623,729 | 11/1986 | Natarajan et al. | 564/155 |
| 4,874,786 | 10/1989 | Menconi et al. | 564/49 |
| 4,904,680 | 2/1990 | Matsui et al. | 564/155 |
| 4,923,890 | 5/1990 | Trainor et al. | 548/538 |
| 4,944,796 | 7/1990 | Wee | 564/155 |
| 5,030,738 | 7/1991 | Reiner | 548/538 |
| 5,128,475 | 7/1992 | Prent | 546/309 |

Primary Examiner—C. Warren Ivy
Assistant Examiner—Raymond Covington
Attorney, Agent, or Firm—Morgan & Finnegan

[57] ABSTRACT

Compounds of formula:

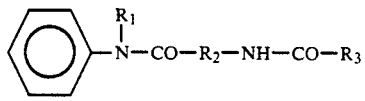

in which $R_1$ is (a) a phenyl radical or a substituted phenyl radical, (b) a chain —CH($R_8$)—COOR$_4$, (c) a chain —CH$_2$—CO—NR$_5$R$_6$ or (d) a phenylalkyl radical, $R_2$ is a methylene or ethylene radical or a radical —CH($R_7$)—, $R_3$ is a 1- or 2-naphthyl radical, 2- or 3-indolyl or phenylamino radical in which the phenyl ring is optionally substituted on the understanding that, when $R_3$ is 1- or 2-naphthyl or 2- or 3-indolyl radical, $R_7$ cannot represent a benzyl, alkylthioalkyl or phenyl radical, as well as, when $R_2$ is a radical —CH($R_7$)—, their racemates and their stereoisomers, and medicinal products containing them.

4 Claims, No Drawings

N-PHENYLAMIDES AND MEDICINAL PRODUCTS CONTAINING THEM

FIELD OF THE INVENTION

The present invention relates to derivatives of formula:

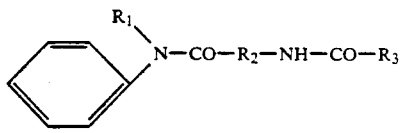

to processes for preparing them and to medicinal products containing them.

In the formula (I), $R_1$ represents:

- a phenyl radical or phenyl radical substituted with an alkyl, alkoxy or cyano radical or with a halogen atom,
- a chain —CH($R_8$)—COOR$_4$ in which $R_4$ represents a hydrogen atom or an alkyl, cycloalkyl, cycloalkylalkyl, phenylalkyl or phenyl radical and $R_8$ represents a hydrogen atom or an alkyl or phenyl radical,
- a chain —CH$_2$—CO—NR$_5$R$_6$ in which $R_5$ and $R_6$, which may be identical or different, represent an alkyl radical or, with the nitrogen atom to which they are attached, form a 1-pyrrolidinyl radical optionally substituted with an alkyl radical, or
- a phenylalkyl radical, $R_2$ represents a methylene or ethylene radical or a radical —CH($R_7$)— in which $R_7$ represents an alkyl radical, benzyl radical, alkylthioalkyl radical in which the alkyl portions contain 1 or 2 carbon atoms or phenyl radical, $R_3$ represents a 1- or 2-naphthyl radical, 2-or 3-indolyl radical or phenylamino radical in which the phenyl ring is optionally substituted with an alkyl, alkoxy, nitro, hydroxyl or alkylthio radical or with 1 or 2 halogen atoms, on the understanding that, when $R_3$ represents a 1- or 2-naphthyl or 2- or 3-indolyl radical, $R_7$ cannot represent a benzyl, alkylthioalkyl or phenyl radical.

In the foregoing definitions and those which will be mentioned below, except where otherwise stated, the alkyl and alkoxy radicals and alkyl and alkoxy portions contain 1 to 4 carbon atoms in a straight or branched chain.

In the formula (I), the halogen atoms are preferably chlorine, bromine or fluorine atoms.

The compounds of formula (I) for which $R_2$ represents a radical —CH($R_7$)— possess isomeric forms. The racemates and enantiomers of these compounds also form part of the invention.

The compounds of formula (I) for which $R_2$ represents a methylene or ethylene radical or a radical —CH($R_7$)— in which $R_7$ represents an alkyl radical, $R_3$ represents a phenylamino radical in which the phenyl ring is optionally substituted with an alkyl, alkoxy, nitro or alkylthio radical or with 1 or 2 halogen atoms, and $R_1$ has the same meanings as above, may be prepared by the action of a derivative of formula:

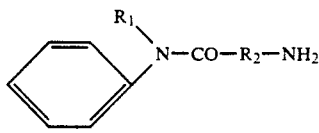

in which $R_2$ has the same meanings as above and $R_1$ has the same meanings as in the formula (I), on a phenyl isocyanate in which the phenyl ring is optionally substituted with an alkyl, alkoxy, nitro or alkylthio radical or with 1 or 2 halogen atoms.

This reaction is generally performed in an inert organic solvent such as tetrahydrofuran, dimethylformamide, a chlorinated solvent (e.g. chloroform, methylene chloride) or an aromatic solvent (e.g. benzene, toluene), at a temperature between 10° C. and the boiling point of the solvent.

The phenyl isocyanates in which the benzene ring is substituted with an alkyl, alkoxy, nitro or alkylthio radical or with 1 or 2 halogen atoms may be obtained by application or adaptation of the method described by R. RICHTER et al., The Chemistry of cyanate and their thio derivatives, S. Patai, Part 2, Wiley N.Y. (1977).

The derivatives of formula (II) may be obtained by application or adaptation of the method described by T. WIELAND et al., Justus Liebigs Ann. Chem., 613, 84 (1958), or by adaptation of GABRIEL's method (GIBSON et al., Angew. Chem. Int. Ed., 7,919 (1968)) which consists in reacting hydrazine hydrate with a compound of formula:

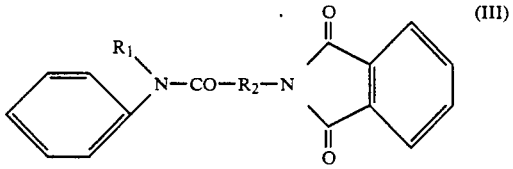

in which $R_1$ and $R_2$ have the same meanings as in the formula (II).

This reaction is preferably performed in an inert solvent such as an alcohol (e.g. methanol, ethanol, propanol), at a temperature between 0° C. and the boiling point of the solvent.

The derivatives of formula (III), with the exception of those for which $R_1$ represents either a chain —CH($R_8$)—COOR$_4$ in which $R_4$ represents a hydrogen atom or a chain —CH$_2$—CO—NR$_5$R$_6$, may be obtained by the action of phthalimide potassium derivative on a derivative of formula:

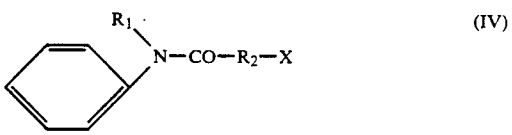

in which $R_1$ has the same meanings as above, $R_2$ has the same meanings as in the formula (III) and X represents a halogen atom, preferably chlorine or bromine.

This reaction is generally performed in an inert solvent such as dimethylformamide or an aromatic solvent (e.g. toluene, xylene), at a temperature in the region of 100° C.

The derivatives of the formula (IV) may be obtained by the action of an amine of formula:

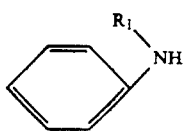

in which $R_1$ has the same meanings as in the formula (IV), on a dihalogenated derivative of formula:

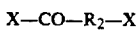

$$X-CO-R_2-X \quad (VI)$$

in which $R_2$ has the same meanings as in the formula (IV) and X represents a halogen atom, preferably chlorine or bromine.

This reaction is preferably performed in the presence of a tertiary amine such as triethylamine, in a chlorinated solvent (e.g. chloroform, methylene chloride, 1,2-dichloroethane), at a temperature between 0° C. and the boiling point of the solvent.

The amines of formula (V) for which $R_1$ represents a phenyl radical substituted with an alkyl, alkoxy or cyano radical or with a halogen atom may be prepared by application or adaptation of the methods described by K. NAKAMURA et al., Synthesis, 882 (1974), J. KULAGOWSKI et al., J. Chem. Soc. Perkin Trans I, 2725 (1985), I. GOLDBERG, Chem. Ber., S.40, 4541 (1907) and R WILLSTATTER et al., Chem Ber., 42, 4135 (1909).

The amines of formula (V) for which $R_1$ represents a phenylalkyl radical may be obtained by application or adaptation of the methods described by SPRINZAK, J. Am. Chem. Soc., 78, 3207 (1956) or SCHELLENBERG, J. Org. Chem., 28, 3259 (1963).

The amines of formula (V) for which $R_1$ represents a chain —CH($R_8$)—COOR$_4$ in which $R_4$ represents an alkyl, cycloalkyl, cycloalkylalkyl, phenylalkyl or phenyl radical and $R_8$ represents a hydrogen atom may be obtained by the action of aniline on a halogenated derivative of formula:

$$X-CH_2-COOR_4 \quad (VII)$$

in which $R_4$ has the same meanings as above and X represents a halogen atom, preferably chlorine or bromine.

This reaction is generally performed in an inert solvent such as a chlorinated solvent (e.g. chloroform, 1,2-dichloroethane, methylene chloride), at the boiling point of the solvent.

The amines of formula (V) for which $R_1$ represents a chain —CH($R_8$)—COOR$_4$ in which $R_8$ represents an alkyl or phenyl radical may be obtained by application or adaptation of the method described by M. JULIA et al., Bull. Soc. Chim. France, 661 (1958).

The halogenated derivatives of formula (VII) may be obtained by application or adaptation of the method described by H. J. BACKER et al., Recueil Trav. Chim. Pays-Bas, 58, 1048 (1939) and in the examples.

The dihalogenated derivatives of formula (VI) for which $R_2$ represents a radical —CH($R_7$) in which $R_7$ represents an alkyl radical may be prepared by halogenation, and preferably by bromination or chlorination, of the corresponding acid.

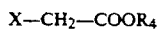

The halogenation is performed by any method known to those skilled in the art for converting an acid to an acid halide. It is especially advantageous to employ phosphorus tribromide, phosphorus oxybromide or thionyl chloride in an inert solvent such as benzene, toluene or chloroform, at a temperature between 10° C. and the boiling point of the solvent.

The derivatives of formula (III) for which $R_1$ represents a chain —CH($R_8$)—COOR$_4$ in which $R_4$ represents a hydrogen atom may be obtained by hydrolysis of the corresponding derivative of formula (III) for which $R_1$ represents a chain —CH($R_8$)—COOR$_4$ in which $R_4$ represents an alkyl radical.

This hydrolysis is performed by any method known to those skilled in the art for converting an ester to a carboxylic acid without affecting the remainder of the molecule. It is especially advantageous to employ trifluoroacetic acid, in a chlorinated inert solvent such as chloroform, dichloromethane or 1,2-dichloroethane, at the boiling point of the solvent.

The derivatives of formula (III) for which $R_1$ represents a chain —CH$_2$—CO—NR$_5$R$_6$ may be obtained by the action of an amine of formula:

in which $R_5$ and $R_6$, which may be identical or different, represent an alkyl radical or, with the nitrogen atom to which they are attached, form a 1-pyrrolidinyl radical optionally substituted with an alkyl radical, on a corresponding derivative of formula (III) for which $R_1$ represents a chain —CH($R_8$)—COOR$_4$ in which $R_4$ and $R_8$ represent a hydrogen atom, or a reactive derivative of this acid.

When acid is employed, the reaction is performed in the presence of a peptide condensing agent such as a carbodiimide (e.g. dicyclohexylcarbodiimide) or N,N'-carbonyldiimidazole, in an inert solvent such as an ether (e.g. THF, dioxane), an amide (e.g. DMF) or a chlorinated solvent (e.g. methylene chloride, dichloroethane, chloroform), at a temperature between 0° C. and the refluxing temperature of the reaction mixture.

When a reactive derivative of the acid is employed, it is possible to react the anhydride, a mixed anhydride, an acid halide or an ester (which can be selected from activated or unactivated esters of the acid).

The reaction is then performed either in an organic medium, optionally in the presence of an acid-acceptor such as a nitrogenous organic base (e.g. a trialkylamine, a pyridine, 1,8-diaz$^a$-bicyclo[5.4.0]undec-7-ene or 1,5-diaz$^a$-bicyclo[4.3.0]non-5-ene), in a solvent such as is mentioned above, or a mixture of these solvents, at a temperature between 0° C. and the refluxing temperature of the reaction mixture, or in a two-phase aqueous-organic medium in the presence of an alkali metal base or alkaline earth metal base (sodium hydroxide, potassium hydroxide) or an alkali metal carbonate or bicarbonate or alkaline earth metal carbonate or bicarbonate, at a temperature of between 0° and 40° C.

The derivatives of formula (III) for which $R_1$ represents an optionally substituted phenyl radical may also be obtained by the action of an amine of formula (V) on a derivative of formula:

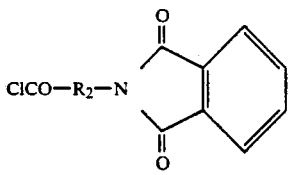

in which R₂ has the same meanings as in the formula (I).

This reaction is preferably performed in an inert solvent such as a chlorinated solvent (e.g. methylene chloride, dichloroethane, chloroform), at a temperature of between 15° and 70° C.

The derivatives of formula (IX) may be prepared by application or adaptation of the method described by W. GRASSMANN et al., Chem. Ber., 83, 244 (1950).

The compounds of formula (I) for which

R₂ represents a methylene or ethylene radical or a radical —CH(R₇)— in which R₇ represents an alkyl radical, R₃ represents a phenylamino radical in which the phenyl ring is optionally substituted with an alkyl, alkoxy, alkylthio, nitro or hydroxyl radical or with 1 or 2 halogen atoms, and R₁ has the same meanings as above, may be prepared by the action of a derivative of formula:

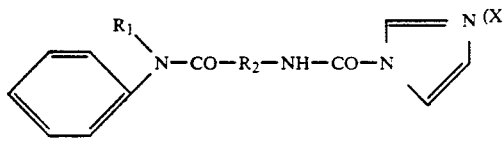

in which R₁ and R₂ have the same meanings as above, on an aniline optionally substituted with an alkyl, alkoxy, alkylthio, nitro or hydroxyl radical or with 1 or 2 halogen atoms.

This reaction is generally performed in an inert solvent such as tetrahydrofuran, dimethylformamide, a chlorinated solvent (e.g. chloroform, dichloromethane, 1,2-dichloroethane) or an aromatic solvent (e.g. benzene, toluene), at a temperature between 20° C. and the boiling point of the solvent.

The substituted anilines may be obtained by application or adaptation of the method described by R. SCHRÖTER, Methoden der Organischen Chemie, Houben Weil, Volume XI/1 p. 360–380.

The derivatives of formula (X) may be obtained by the action of a derivative of formula (II) on N,N'-carbonyldiimidazole.

This reaction is performed in the same solvents as those mentioned above for the reaction of a compound of formula (X) with an aniline, at a temperature of between 15° and 50° C.

It is possible not to isolate the compound of formula (X), and to react it in situ with an aniline.

The compounds of formula (I) for which

R₂ represents a methylene or ethylene radical or a radical —CH(R₇)— in which R₇ represents an alkyl radical, R₃ represents a 1- or 2-naphthyl or 2- or 3-indolyl radical, and R₁ has the same meanings as above, may be obtained by the action of a derivative of formula (II) in which R₁ and R₂ have the same meanings as above, on a derivative of formula:

$$HOOC-R_3 \qquad (XI)$$

in which R₃ represents a 1- or 2-naphthyl or 2- or 3-indolyl radical, or a reactive derivative of this acid.

This reaction is performed under the same conditions as those described above for the reaction of an amine of formula (VIII) with a derivative of formula (III).

The compounds of formula (I) for which

R₃ represents a phenylamino radical in which the phenyl ring is optionally substituted with an alkyl, alkoxy, nitro or alkylthio radical or with 1 or 2 halogen atoms, R₂ has the same meanings as above, R₁ has the same meanings as above with the exception of representing a chain —CH(R₈)—COOR₄ in which R₄ represents a hydrogen atom or a chain —CH₂—CO—NR₅R₆, may be obtained by the action of an amine of formula (V) in which R₁ has the same meanings as in the formula (I), on a derivative of the formula:

$$HOOC-R_2-NH-CO-R_3 \qquad (XII)$$

in which R₃ represents a phenylamino radical in which the phenyl ring is optionally substituted with an alkyl, alkoxy, nitro or alkylthio radical or with 1 or 2 halogen atoms and R₂ has the same meanings as in the formula (I).

This reaction is preferably performed in the presence of thionyl chloride, in a chlorinated solvent (e.g. chloroform, methylene chloride, 1,2-dichloroethane), at the boiling point of the solvent.

The derivatives of formula (XII) may be obtained by the action of an amino acid of formula:

$$HOOC-R_2-NH_2 \qquad (XIII)$$

in which R₂ has the same meanings as in the formula (XII), on a phenyl isocyanate in which the phenyl ring is optionally substituted with an alkyl, alkoxy, nitro or alkylthio radical or with 1 or 2 halogen atoms.

This reaction is generally performed in water, in the presence of a base such as an alkali metal carbonate (e.g. sodium or potassium bicarbonate), at a temperature in the region of 20° C.

The compounds of formula (I) for which

R₃ represents a phenylamino radical in which the phenyl ring is optionally substituted with an alkyl, alkoxy, nitro or alkylthio radical or with 1 or 2 halogen atoms, R₂ has the same meanings as above, and R₁ represents a chain —CH(R₈)—COOR₄ in which R₄ represents a hydrogen atom, may be obtained by hydrolysis of the corresponding derivative of formula (I) for which R₁ represents a chain —CH(R₈)—COOR₄ in which R₄ represents an alkyl radical.

This hydrolysis is performed by any method known to those skilled in the art for converting an ester to a carboxylic acid without affecting the remainder of the molecule. It is especially advantageous to employ trifluoroacetic acid, in a chlorinated inert solvent such as chloroform, dichloromethane or 1,2-dichloroethane, at the boiling point of the solvent.

The compounds of formula (I) for which

R₃ represents a phenylamino radical in which the phenyl ring is optionally substituted with an alkyl, alkoxy, nitro or alkylthio radical or with 1 or 2 halogen atoms, $R_2$ has the same meanings as above, and $R_1$ represents a chain $—CH_2—CO—NR_5R_6$, may be obtained by the action of an amine of formula (VIII) on a corresponding acid of formula (I) for which $R_1$ represents a chain $—CH(R_8)—COOR_4$ in which $R_4$ represents a hydrogen atom, or a reactive derivative of this acid.

This reaction is performed under the conditions described above for the preparation of the compounds of formula (III) in which $R_1$ represents a chain $—CH_2—CO—NR_5R_6$.

The compounds of formula (I) for which $R_3$ represents a phenylamino radical in which the phenyl ring is substituted with a hydroxyl radical may be obtained by dealkylation of a corresponding derivative of formula (I) for which $R_3$ represents a phenylamino radical in which the phenyl ring is substituted with an alkoxy radical.

This dealkylation is generally performed by means of a methylene chloride solution of boron tribromide in a chlorinated solvent (e.g. chloroform, methylene chloride, 1,2-dichloroethane), at a temperature of between $-50°$ C. and $+20°$ C.

The compounds of formula (I) for which $R_1$ represents a chain $—CH(R_8)—COOR_4$ in which $R_4$ represents a phenyl radical may also be prepared by the action of phenol on a corresponding compound of formula (I) for which $R_4$ represents a hydrogen atom.

This reaction is generally performed in an inert solvent such as a chlorinated solvent (e.g. chloroform, methylene chloride), in the presence of a base such as a trialkylamine and of 1-benzotriazolyloxytris(dimethylamino)phosphonium hexafluorophosphonate, at a temperature in the region of 25° C.

The enantiomers of the compounds of formula (I) for which $R_2$ represents a radical $—CH(R_7)—$ may be obtained by resolution of the racemates, e.g. by chromatography on a chiral column according to W. H. PIRCKLE et al., Asymmetric Synthesis, Vol. 1, Academic Press (1983), or by synthesis from chiral precursors.

The compounds of formula (I) may be purified by the usual known methods, e.g. by crystallization, chromatography or extractions.

The compounds of formula (I) have advantageous pharmacological properties. These compounds possess a strong affinity for cholecystokinin (CCK) receptors, and are hence useful in the treatment and prevention of disorders linked to CCK in respect of the nervous system and the gastrointestinal apparatus.

Thus, these compounds may be used for the treatment or prevention of psychoses, the anxiety disorders of Parkinson's disease, tardive dyskinesia, irritable colon syndrome, acute pancreatitis, ulcers, disorders of intestinal motility and some tumors of the lower oesophagus, colon and intestine, and as an appetite regulator.

These compounds also have a potentiating effect on the analgesic activity of narcotic and non-narcotic medicinal products.

The affinity of the compounds of formula (I) for CCK receptors was determined according to a technique based on that of A. SAITO et al., J. Neuro. Chem., 37, 483–490 (1981).

In this test, the $IC_{50}$ of the compounds of formula (I) is less than or equal to 1,000 nM.

The compounds of formula (I) have low toxicity. Administered subcutaneously to mice, their $LD_{50}$ is generally above 40 mg/kg.

Of special interest are the compounds of formula (I) for which $R_1$ represents a phenyl radical optionally substituted with an alkoxy radical or a halogen atom or a chain $—CH(R_8)—COOR_4$ in which $R_4$ represents an alkyl or cycloalkylalkyl radical and $R_8$ represents a hydrogen atom or a phenyl radical, and $R_2$ and $R_3$ are as defined above.

Preferred compounds are the following:

2-[3-(3-methylthiophenyl)ureido]-N,N-didphenylacetamide,

3-[3-(3-methylphenyl)ureido]-N,N-diphenylpropionamide, tert-butyl 2-{2-[3-(3-methylphenyl)ureido]-N-phenylacetamido}acetate, tert-butyl (RS)-N-{2-[3-(3-methylphenyl)ureido]-3-phenylpropionyl}-N-phenylglycinate, 2-[3-(2,3-dichlorophenyl)ureido]-N,N-diphenylacetamide, ethyl (RS)-2-{2-[3-(3-methylphenyl)ureido]-N-phenylacetamido}phenylacetate, N-(3-chlorophenyl)-2-[3-(3-methylphenyl)ureido]-N-phenylacetamide, N-(4-methoxyphenyl)-N-phenyl-2-[3-(3-methylphenyl)ureido]acetamide, tert-butyl N-{2-[3-(3-methylthiophenyl)ureido]acetyl}-N-phenylglycinate, tert-butyl N-{2-[3-(3-methoxyphenyl)ureido]acetyl)-N-phenylglycinate, N-[N-(tert-butoxycarbonylmethyl)phenylcarbamoylmethyl]-2-indolecarboxamide, tert-butyl N-[N-(3,4-dichlorobenzoyl)glycyl]-N-phenylglycinate, tert-butyl N-[N-(2-naphthoyl)glycyl]-N-phenylglycinate, cyclopropylmethyl 2-{2-[3-(3-methylphenyl)ureido]-N-phenylacetamido}acetate, (RS)-sec-butyl 2-{2-[3-(3-methylphenyl)ureido]-N-phenylacetamido)acetate.

EXAMPLES

The examples which follow illustrate the invention without limiting the latter.

EXAMPLE 1

3-Methylphenyl isocyanate (0.59 g) is added at a temperature in the region of 25° C. to a solution of 2-amino-N,N-diphenylacetamide (1 g) in anhydrous tetrahydrofuran (20 cc). The suspension obtained is stirred for 4 hours at a temperature in the region of 25° C. and the insoluble product is separated by filtration. After recrystallization in acetonitrile, N,N-diphenyl-2-[3-(3-methylphenyl)ureido]acetamide (0.8 g), m.p. 240° C., is obtained.

2-Amino-N,N-diphenylacetamide may be prepared according to the method described by T. WEILAND and H. URBACH, Justus Liebigs Ann. Chem., 613, 84 (1958).

EXAMPLE 2

Working in a manner similar to that described in Example 1, but starting with 2-amino-N,N-diphenylacetamide (1 g) and phenyl isocyanate (0.59 g), and after recrystallization in a mixture of dimethylformamide and acetonitrile (20:80 by volume), N,N-diphenyl-2-(3-phenylureido)acetamide (1.2 g), m.p. 240° C., is obtained.

EXAMPLE 3

Working in a manner similar to that described in Example 1, but starting with 2-amino-N,N-diphenylacetamide (2 g) and 3-methoxyphenyl isocyanate (1.3 g), and after recrystallization in acetonitrile, 2-[3-(3-methoxyphenyl)ureido]-N,N-diphenylacetamide (2.6 g), m.p. 182° C., is obtained.

EXAMPLE 4

A 1M methylene chloride solution (25 cc) of boron tribromide is added in the course of 15 minutes at a temperature in the region of −50° C. to a solution, maintained under a nitrogen atmosphere, of 2-[3-(3-methoxyphenyl)ureido]-N,N-diphenylacetamide (1.6 g) in dichloromethane (25 cc). The mixture obtained is stirred for 2 hours at a temperature in the region of −50° C. and then for 20 hours at a temperature in the region of 20° C. The precipitate formed is separated by filtration, washed with distilled water (6×10 cc) and dried in the air. After recrystallization in acetonitrile, 2-[3-(3-hydroxyphenyl)ureido]-N,N-diphenylacetamide (0.5 g), m.p. 244° C., is obtained.

EXAMPLE 5

N,N,'-Carbonyldiimidazole (0.72 g) is added to a solution of 2-amino-N,N-diphenylacetamide (1 g) in anhydrous tetrahydrofuran (15 cc). The solution is stirred for 2 hours at a temperature in the region of 25° C. and 3-methylthioaniline (1.2 g) is then added. The solution obtained is stirred under reflux for 12 hours and then concentrated to dryness under reduced pressure (2.7 kPa). The residue obtained is taken up with distilled water (60 cc) and stirred for 30 minutes at a temperature in the region of 20° C. The insoluble product is separated by filtration, washed with distilled water and dried in the air. After recrystallization in acetonitrile, 2-[3-(3-methylthiophenyl)ureido]-N,N-diphenylacetamide (1 g), m.p. 182° C., is obtained.

EXAMPLE 6

3-Nitroaniline (2.8 g) is added to a solution of N-(diphenylcarbamoylmethyl)-1-imidazolecarboxamide (3.2 g) in anhydrous toluene (35 cc). The solution obtained is stirred under reflux for 4 hours. After cooling, the reaction mixture is washed with an N aqueous solution (40 cc) of methanesulphonic acid and distilled water (2×30 cc). The organic phase is dried over magnesium sulphate, filtered and concentrated to dryness under reduced pressure (2.7 kPa) at 40° C. The residue is stirred for 20 minutes in dichloromethane (25 cc). The insoluble product is separated by filtration, washed with dichloromethane (5 cc) and dried in the air. After recrystallization in ethyl acetate, 2-[3-(3-nitrophenyl)ureido]-N,N-diphenylacetamide (0.7 g), m.p. 180° C., is obtained.

N-(Diphenylcarbamoylmethyl)-1-imidazolecarboxamide may be prepared in the following manner: a solution of 2-amino-N,N-diphenylacetamide (10.2 g) in anhydrous tetrahydrofuran (30 cc) is run into a solution of N,N'-carbonyldiimidazole (7.3 g) in anhydrous tetrahydrofuran (100 cc). The solution obtained is stirred for 3 hours at a temperature in the region of 25° C. and then concentrated to dryness under reduced pressure (2.7 kPa) at 40° C. The residue is dissolved in ethyl acetate (150 cc) and the solution obtained is washed with distilled water (2×100 cc), dried over magnesium sulphate and concentrated to dryness under reduced pressure (2.7 kPa) at 40° C. N-(Diphenylcarbamoylmethyl)-1-imidazolecarboxamide (14 g), m.p. 162° C., is thereby obtained.

EXAMPLE 7

Working in a manner similar to that described in Example 1, but starting with (RS)-2-amino-N,N-diphenylpropionamide (1.2 g) and 3-methylphenyl isocyanate (0.66 g), and after recrystallization in methanol, (RS)-2-[3-(3-methylphenyl)ureido]-N,N-diphenylpropionamide (0.8 g), m.p. 197° C., is obtained.

(RS)-2-Amino-N,N-diphenylpropionamide may be prepared in the following manner: hydrazine hydrate (2.9 g) is added to a solution of (RS)-2-phthalimido-N,N-diphenylpropionamide (10.7 g) in methanol (150 cc). The solution obtained is stirred under reflux for 3 hours and then poured into 4N aqueous hydrochloric acid solution (150 cc). The insoluble product is separated by filtration and the filtrate is concentrated to a volume of approximately 120 cc under reduced pressure (2.7 kPa) at 40° C. After neutralization with 4N aqueous sodium hydroxide solution, the solution is extracted with ethyl acetate (3×50 cc). The combined organic phases are washed with distilled water (4×50 cc), dried over magnesium sulphate and then concentrated to dryness under reduced pressure (2.7 kPa) at 40° C. (RS)-2-Amino-N,N-diphenylpropionamide (5.8 g), m.p. 82° C., is thereby obtained.

(RS)-2-Phthalimido-N,N-diphenylpropionamide may be prepared in the following manner: phthalimide potassium derivative (12.6 g) is added to a solution of (RS)-2-chloro-N,N-diphenylpropionamide (8.9 g) in dimethylformamide (160 cc). The mixture is stirred at a temperature in the region of 100° C. for 5 hours and then poured into distilled water (1,500 cc). The insoluble product is separated by filtration, washed with distilled water (3×60 cc) and dried in the air. (RS)-2-Phthalimido-N,N-diphenylpropionamide (10.7 g), m.p. 152° C., is thereby obtained.

(RS)-2—Chloro-N,N-diphenylpropionamide may be prepared in the following manner: 2-chloropropionyl chloride (10.2 g) is added to a solution, maintained at a temperature in the region of 15° C., of diphenylamine (10.2 g) and triethylamine (8 g) in 1,2-dichloroethane (60 cc). The mixture is stirred for 6 hours at a temperature in the region of 60° C. After cooling, it is washed with distilled water (3×100 cc). The organic phase is dried over magnesium sulphate and concentrated to dryness under reduced pressure (2.7 kPa) at 40° C. (RS)-2-Chloro-N,N-diphenylpropionamide (8.9 g), m.p. 89° C., is thereby obtained.

EXAMPLE 8

Working in a manner similar to that described in Example 1, but starting with 3-amino-N,N-diphenylpropionamide (1 g) and 3-methylphenyl isocyanate (0.55 g), and after recrystallization in acetonitrile, 3-[3-(3-methylphenyl)ureido]-N,N-diphenylpropionamide (0.85 g), m.p. 179° C., is obtained.

3-Amino-N,N-diphenylpropionamide may be prepared in a manner similar to that described in Example 7 for the preparation of 2-amino-N,N-diphenylpropionamide, but starting with 3-phthalimido-N,N-diphenylpropionamide (8.4 g) and hydrazine hydrate (2.3 g). 3-Amino-N,N-diphenylpropionamide (3.9 g), m.p. 50° C., is thereby obtained.

3-Phthalimido-N,N-diphenylpropionamide may be prepared in a manner similar to that described in Example 7 for the preparation of (RS)-2-phthalimido-N,N-diphenylpropionamide, but starting with 3-chloro-N,N-diphenylpropionamide (6.3 g) and phthalimide potassium derivative (9 g). 3-Phthalimido-N,N-diphenylpropionamide (8.5 g), m.p. 140° C., is thereby obtained.

3-Chloro-N,N-diphenylpropionamide may be prepared in a manner similar to that described in Example 7 for the preparation of (RS)-2-chloro-N,N-diphenylpropionamide, but starting with diphenylamine (8.5 g), triethylamine (7.1 g) and 3-chloropropionyl chloride (8.8 g). 3-Chloro-N,N-diphenylpropionamide (6.3 g), m.p. 92° C., is thereby obtained.

EXAMPLE 9

Oxalyl dichloride (1.7 g), dissolved in anhydrous diethyl ether (5 cc), is added at a temperature in the region of 10° C. to a solution, maintained under a nitrogen atmosphere, of 2-indolecarboxylic acid (2.15 g) and dimethylformamide (0.1 cc) in anhydrous diethyl ether (30 cc). The solution obtained is stirred for 2 hours at a temperature in the region of 20° C. and then added dropwise to a solution of 2-amino-N,N-diphenylacetamide (1.3 g) and triethylamine (1.2 g) in 1,2-dichloroethane (30 cc). The suspension obtained is stirred for 18 hours at a temperature in the region of 20° C. and then poured into distilled water (60 cc). The insoluble product is separated by filtration, washed with distilled water and dried in the air. After recrystallization in a mixture of dimethylformamide and acetonitrile (1:25 by volume), N-(diphenylcarbamoylmethyl)-2-indolecarboxamide (1 g), m.p. 218° C., is obtained.

EXAMPLE 10

Working in a manner similar to that described in Example 9, but starting with 2-naphthalenecarboxylic acid (0.95 g), oxalyl dichloride (0.7 g), 2-amino-N,N-diphenylacetamide (1.2 g) and triethylamine (0.8 g), and after recrystallization in acetonitrile, N-(diphenylcarbamoylmethyl)-2-naphthalenecarboxamide (1.2 g), m.p. 205° C., is obtained.

EXAMPLE 11

Working in a manner similar to that described in Example 9, but starting with 2-indolcarboxylic acid (1.3 g), oxalyl dichloride (1 g) and (RS)-2-amino-N,N-diphenylpropionamide (1.2 g), and after recrystallization in acetonitrile, (RS)-N-(1-diphenylcarbamoylethyl)-2-indolcarboxamide (1.6 g), m.p. 242° C., is obtained.

EXAMPLE 12

Working in a manner similar to that described in Example 1, but starting with tert-butyl 2-(2-amino-N-phenylacetamido)acetate (1.25 g) and 3-methylphenyl isocyanate (0.63 g), and after recrystallization in acetonitrile, tert-butyl 2-{2-[3-(3-methylphenyl)ureido]-N-phenylacetamido}acetate (0.8 g), m.p. 180° C., is obtained.

tert-Butyl 2-(2-amino-N-phenylacetamido)acetate may be prepared in the following manner: hydrazine hydrate (0.25 g) is added to a solution of tert-butyl 2-(2-phthalimido-N-phenylacetamido)acetate (2 g) in methanol (20 cc). The reaction mixture is stirred under reflux for 1 hour and the insoluble product is then separated by filtration. The filtrate is concentrated to dryness under reduced pressure (2.7 kPa) at 30° C. The residue obtained is stirred with diisopropyl ether (25 cc) and the insoluble product is separated by filtration. The filtrate is concentrated to dryness under reduced pressure (2.7 kPa) at 30° C. tert-Butyl 2-(2-amino-N-phenylacetamido)acetate (0.8 g) is thereby obtained in the form of a yellow oil.

tert-Butyl 2-(2-phthalimido-N-phenylacetamido)acetate may be prepared in a manner similar to that described in Example 7 for the preparation of (RS)-2-phthalimido-N,N-diphenylpropionamide, but starting with tert-butyl 2-(2-chloro-N-phenylacetamido)acetate (8.9 g) and phthalimide potassium derivative (12.8 g). tert-Butyl 2-(2-phthalimido-N-phenylacetamido)acetate (8.8 g), m.p. 126° C., is thereby obtained.

tert-Butyl 2-(2-chloro-N-phenylacetamido)acetate may be prepared in a manner similar to that described in Example 7 for the preparation of (RS)-2-chloro-N,N-diphenylpropionamide, but starting with tert-butyl N-phenylglycinate (21.6 g) and chloroacetyl chloride (17.8 g). tert-Butyl 2-(2-chloro-N-phenylacetamido)acetate (9 g), m.p. 86° C., is thereby obtained.

tert-Butyl N-phenylglycinate may be prepared in the following manner: tert-butyl bromoacetate (58 g) is added to a solution of aniline (56 g) in 1,2-dichloroethane (600 cc). The solution obtained is stirred under reflux for 48 hours. After cooling, the insoluble product is separated by filtration and the filtrate is washed with 0.1N aqueous hydrochloric acid solution (200 cc) and with distilled water (3×200 cc). The organic phase is dried over magnesium sulphate and then concentrated to dryness under reduced pressure (2.7 kPa) at 40° C. tert-Butyl N-phenylglycinate (54 g) is thereby obtained in the form of a brown oil.

EXAMPLE 13

Working in a manner similar to that described in Example 1, but starting with 2-amino-N-phenyl-N-[2-oxo-2-(1-pyrrolidinyl)ethyl]acetamide (0.7 g) and 3-methylphenyl isocyanate (0.36 g), and after recrystallization in acetonitrile, 2-[3-(3-methylphenyl)ureido]-N-phenyl-N-[2-oxo-2-(1-pyrrolidinyl) ethyl]acetamide (0.55 g), m.p. 206° C., is obtained.

2-Amino-N-phenyl-N-[2-oxo-2-(1-pyrrolidinyl)ethyl]acetamide may be prepared in a manner similar to that described in Example 7 for the preparation of (RS)-2-amino-N,N-diphenylpropionamide, but starting with 2-phthalimido-N-phenyl-N-[2-oxo-2-(1-pyrrolidinyl)ethyl]acetamide (1.9 g) and hydrazine hydrate (0.49 g). 2-Amino-N-phenyl-N-[2-oxo-2-(1-pyrrolidinyl)ethyl]acetamide (0.7 g) is thereby obtained in the form of a yellow oil.

2-Phthalimido-N-phenyl-N-[2-oxo-2-(1-pyrrolidinyl)ethyl]acetamide may be prepared in the following manner; N,N'-carbonyldiimidazole (1 g) is added to a suspension of 2-(2-phthalimido-N-phenylacetamido)acetic acid (2 g) in anhydrous tetrahydrofuran (20 cc). The mixture is stirred for 2 hours at a temperature in the region of 25° C. and pyrrolidine (0.46 g) is then added. The solution obtained is stirred under reflux for 1 hour and then concentrated to dryness under reduced pressure (2.7 kPa) at 40° C. The residue is dissolved in ethyl acetate (40 cc) and the solution obtained is washed with N aqueous hydrochloric acid solution (20 cc) and then distilled water (2×20 cc). The organic phase is dried over magnesium sulphate and then concentrated to dryness under reduced pressure (2.7 kPa) at 40° C. 2-Phthalimido-N-phenyl-N-[2-oxo-2-(1-pyrrolidinyl)e- thyl]acetamide (2 g) is thereby obtained in the form of an amorphous white powder.

2-(2-Phthalimido-N-phenylacetamido)acetic acid may be prepared in the following manner: trifluoroacetic acid (17.9 g) is added to a solution of tert-butyl 2-(2-phthalimido-N-phenylacetamido)acetate (8 g) in dichloromethane (30 cc). The solution obtained is stirred under reflux for 1 hour and then concentrated to dryness under reduced pressure (2.7 kPa) at 40° C. After recrystallization in diisopropyl ether, 2-(2-phthalimido-N-phenylacetamido)acetic acid (5.9 g), m.p. 224° C., is obtained.

EXAMPLE 14

Working in a manner similar to that described in Example 1, but starting with 2-amino-N-benzyl-N-phenylacetamide (1.9 g) and 3-methylphenyl isocyanate (1.1 g), and after recrystallization in acetonitrile, N-benzyl-N-phenyl-2-[3-(3-methylphenyl)ureido]acetamide (2.3 g), m.p. 175° C., is obtained.

2-Amino-N-benzyl-N-phenylacetamide may be prepared in a manner similar to that described in Example 7 for the preparation of (RS)-2-amino-N,N-diphenylpropionamide, but starting with 2-phthalimido-N-benzyl-N-phenylacetamide (12.5 g) and hydrazine hydrate (3.44 g). 2-Amino-N-benzyl-N-phenylacetamide (8.1 g) is thereby obtained in the form of a yellow oil.

2-Phthalimido-N-benzyl-N-phenylacetamide may be prepared in a manner similar to that described in Example 7 for the preparation of (RS)-2-phthalimido-N,N-diphenylpropionamide, but starting with N-benzyl-2-chloro-N-phenylacetamide (10.3 g) and phthalimide potassium derivative (14.8 g). 2-Phthalimido-N-benzyl-N-phenylacetamide (12.5 g), m.p. 150° C., is thereby obtained.

N-Benzyl-2-chloro-N-phenylacetamide may be prepared according to the method described by Y. V. SVETKIN and A. N. MINLIBAEVA, Zh. Obshch. Khim., 33(4), 1108 (1963) (C.A. 59, 9920a (1963)).

EXAMPLE 15

A suspension of (RS)-2-[3-(3-methylphenyl)ureido]-4-(methylthio)butanoic acid (4.5 g) and tert-butyl anilinoacetate (3.3 g) in anhydrous 1,2-dichloroethane (300 cc) is heated to reflux until a solution is obtained. Thionyl chloride (1.16 cc) is then added, refluxing being maintained until the gaseous evolution has ceased. The reaction mixture is then poured into a saturated aqueous sodium bicarbonate solution (100 cc) and the organic phase is washed with water (100 cc), dried over magnesium sulphate and concentrated to dryness under reduced pressure (2.7 kPa) at 40° C. The oily residue obtained is purified by chromatography on silica gel (0.04–0.063 mm; 350 g) contained in a column 5 cm in diameter [eluant: methylene chloride/methanol (98:2 by volume)], using an excess pressure of 40 kPa of nitrogen and collecting 100-cc fractions. Fractions 12 to 28 are combined and concentrated to dryness under reduced pressure (2.7 kPa) at 40° C. By recrystallization of the residue thereby obtained in diethyl ether, tert-butyl (RS)-N-{2-[3-(3-methylphenyl)ureido]-4-methylthiobutyryl}-N-phenylglycinate (2.8 g), m.p. 142° C., is obtained.

(RS)-2-[3-(3-Methylphenyl)ureido]-4-(methylthio)butanoic acid may be prepared in the following manner: 3-methylphenyl isocyanate (5.2 g) is added at a temperature in the region of 20° C. to a suspension of DL-methionine (6 g) and sodium bicarbonate (3.36 g) in distilled water (60 cc), and the mixture is stirred for 16 hours at a temperature in the region of 20° C. The insoluble product is then separated by filtration and the filtrate acidified to pH 1 using 4N aqueous hydrochloric acid solution. The solid obtained is separated by filtration, washed with water and dried in the air. (RS)-2-[3-(3-Methylphenyl)ureido]-4-(methylthio)butanoic acid (9.6 g), m.p. 143° C., is thereby obtained.

EXAMPLE 16

Working as in Example 15, but starting with (RS)-2-[3-(3-methylphenyl)ureido]-3-phenylpropanoic acid (4.8 g) and tert-butyl anilinoacetate (3.3 g) in anhydrous 1,2-dichloroethane (300 cc) and thionyl chloride (1.16 cc), and recrystallizing successively in diethyl ether and then in isopropanol, tert-butyl (RS)-N-{2-[3-(3-methylphenyl)ureido]-3-phenylpropionyl}-N-phenylglycinate (3.2 g), m.p. 198° C., is obtained.

(RS)-2-[3-(3-Methylphenyl)ureido]-3-phenylpropanoic acid may be prepared in a manner similar to that described in Example 15 for the preparation of (RS)-2-[3-(3-methylphenyl)ureido]-4-(methylthio)butanoic acid, but starting with DL-phenylalanine (6.6 g), sodium bicarbonate (3.36 g), water (100 cc) and 3-methylphenyl isocyanate (5.3 g). (RS)-2-[3-(3-Methylphenyl)ureido]-3-phenylpropanoic acid (9.7 g), m.p. 182° C., is thereby obtained.

EXAMPLE 17

A solution of 2-amino-N,N-diphenylacetamide (4.53 g) in anhydrous 1,2-dichloroethane (50 cc) is added to a solution of N,N'-carbonyldiimidazole (3.6 g) in anhydrous 1,2-dichloroethane (80 cc). The solution obtained is stirred for 2 hours at a temperature in the region of 20° C., 2,3-dichloroaniline (6.4 g) is then added and the mixture is stirred for 20 hours under reflux. After cooling, the reaction mixture is washed with water (3×75 cc). The organic phase is dried over magnesium sulphate and concentrated to dryness under reduced pressure (2.7 kPa). The oily residue obtained is purified by chromatography on silica gel (0.04–0.063 mm; 250 g) contained in a column 4.2 cm in diameter [eluant: methylene chloride/methanol (98:2 by volume)], using an excess pressure of 40 kPa of nitrogen and collecting 20-cc fractions. Fractions 11 to 20 are combined and concentrated to dryness under reduced pressure (2.7 kPa) at 40° C. and the residue obtained is recrystallized in dioxane. [3-(2,3-Dichlorophenyl)ureido]-N,N-diphenylacetamide (1.4 g), m.p. 210° C., is thereby obtained.

EXAMPLE 18

Working in a manner similar to that described in Example 15, but starting with 2-[3-(3-methylphenyl)ureido]acetic acid (1.56 g), ethyl (RS)-2-anilinopropionate (1.45 g) in anhydrous 1,2-dichloroethane (30 cc) and thionyl chloride (0.89 g), and after recrystallization in a mixture of ethyl acetate and isopropyl ether (12:1 by volume), ethyl (RS)-2-{2-[3-(3-methylphenyl)ureido]-N-phenylacetamido}propionate (1 g), m.p. 113°–8° C., is obtained.

Ethyl (RS)-2-anilinopropionate may be prepared according to the method described by M. JULIA and G. TCHERNOFF, Bull. Soc. Chim. France, 661 (1958).

EXAMPLE 19

Working in a manner similar to that described in Example 15, but starting with 2-[3-(3-methylphenyl- )ureido]acetic acid, ethyl (RS)-2-anilinophenylacetate (1.15 g) in anhydrous 1,2-dichloroethane (15 cc) and thionyl chloride (0.53 g), and after recrystallization in acetonitrile, ethyl (RS)-2-{2-[3-(3-methylphenyl-)ureido]-N-phenylacetamido}phenylacetate (1.1 g), m.p. 120° C., is obtained.

Ethyl (RS)-2-anilinophenylacetate may be prepared according to the method described by M. JULIA and G. TCHERNOFF, Bull. Soc. Chim. France, 661 (1958).

EXAMPLE 20

Phenyl isocyanate (1.06 g) is added at a temperature in the region of 20° C. to a solution of 2-amino-N-(3-chlorophenyl)-N-phenylacetamide (2 g) in anhydrous tetrahydrofuran (30 cc). The suspension obtained is stirred for 3 hours at a temperature in the region of 20° C. and then concentrated to dryness under reduced pressure (2.7 kPa) at 40° C. After recrystallization of the residue in acetonitrile, N-(3-chlorophenyl)-2-[3-(3-methylphenyl)ureido]-N-phenylacetamide (2.3 g), m.p. 184° C., is thereby obtained.

2-Amino-N-(3-chlorophenyl)-N-phenylacetamide may be prepared in the following manner: hydrazine hydrate (1.33 g) is added to a solution of 2-phthalimido-N-(3-chlorophenyl)-N-phenylacetamide (5.2 g) in methanol (40 cc). The reaction mixture is stirred under reflux for 3 hours, then cooled to a temperature in the region of 20° C. and treated with 5N aqueous hydrochloric acid solution to a pH in the region of 1. The insoluble product is separated by filtration and removed; the filtrate is concentrated to dryness under reduced pressure (2.7 kPa) at 40° C. The residual oil is dissolved in ethyl acetate (50 cc) and the solution obtained is treated with distilled water (50 cc) and then with 1N aqueous sodium hydroxide solution (50 cc) to a pH in the region of 8. The aqueous phase is separated after settling has taken place and then re-extracted with ethyl acetate (2×30 cc). The organic phases are combined, washed with distilled water (2×10 cc), dried over magnesium sulphate, filtered and concentrated to dryness under reduced pressure (2.7 kPa) at 40° C. 2-Amino-N-(3-chlorophenyl)-N-phenylacetamide (1 g) is thereby obtained in the form of a yellow oil, which is used in the subsequent syntheses without further treatment.

2-Phthalimido-N-(3-chlorophenyl)-N-phenylacetamide may be prepared in the following manner: triethylamine (4.2 g) is added to a solution, maintained under an argon atmosphere, of 3-chlorodiphenylamine (6.1 g) in 1,2-dichloroethane (50 cc), and this is followed by the dropwise addition, at a temperature in the region of 20° C., of a solution of 2-phthalimidoacetyl- chloride (9.7 g) in 1,2-dichloroethane (20 cc). The solution obtained is stirred for 4 hours at a temperature in the region of 20° C. and then for 1 hour at 60° C., cooled to a temperature in the region of 20° C. and treated with distilled water (50 cc). The aqueous phase is separated after settling has taken place and then re-extracted with 1,2-dichloroethane (2×30 cc). The organic phases are combined, washed with distilled water (2×20 cc), dried over magnesium sulphate, filtered and then concentrated to dryness under reduced pressure (2.7 kPa) at 40° C. After recrystallization in a mixture of ethyl acetate and diisopropyl ether (70:30 by volume), 2-phthalimido-N-(3-chlorophenyl)-N-phenylacetamide (5.4 g), m.p. 185° C., is thereby obtained.

2-Phthalimidoacetyl chloride may be prepared according to the method described by W. GRASSMANN et al., Chem. Ber., 83, 244 (1950).

EXAMPLE 21

Working in a manner similar to that described in Example 20, but starting with 2-amino-N-(4-methoxyphenyl)-N-phenylacetamide (2.9 g) and phenyl isocyanate (1.65 g), and after recrystallization in ethyl acetate, N-(4-methoxyphenyl)-N-phenyl-2-[3-(3-methylphenyl)ureido]acetamide (1.78 g), m.p. 182° C., is obtained.

2-Amino-N-(4-methoxy-phenyl)-N-phenylacetamide may be prepared in a manner similar to that described in Example 20 for the preparation of 2-amino-N-(3-chlorophenyl)-N-phenylacetamide, but starting with 2-phthalimido-N-(4-methoxyphenyl)-N-phenylacetamide (5 g) and hydrazine hydrate (1.3 g). 2-Amino-N-(4-methoxyphenyl)-N-phenylacetamide (3.1 g) is thereby obtained in the form of an oil, which is used in the subsequent syntheses without further treatment.

2-Phthalimido-N-(4-methoxyphenyl)-N-phenylacetamide may be prepared in a manner similar to that described in Example 20 for the preparation of 2-phthalimido-N-(3-chlorophenyl)-N-phenylacetamide, but starting with 4-methoxy-diphenylamine (6 g), triethylamine (4 g) and 2-phthalimidoacetyl chloride (8.7 g). After recrystallization in ethyl acetate, 2-phthalimido-N-(4-methoxyphenyl)-N-phenylacetamide (5.1 g), m.p. 192° C., is thereby obtained.

4-Methoxydiphenylamine may be prepared according to the method described by R. WILLSTATTER and H. KUBLI, Chem. Ber., 42, 4135–4151 (1909).

EXAMPLE 22

Working in a manner similar to that described in Example 1, but starting with 2-(2-amino-N-phenylacetamido)-N,N-dipropylacetamide (1.7 g) and 3-methylphenyl isocyanate (0.77 g), and after recrystallization in acetonitrile, 2-{2-[3-(3-methylphenyl-)ureido]-N-phenylacetamido}-N,N-dipropylacetamide (1.1 g), m.p. 182° C., is obtained.

2-(2-Amino-N-phenylacetamido)-N,N-dipropylacetamide may be prepared in a manner similar to that described in Example 7 for the preparation of 2-amino-N,N-diphenylpropionamide, but starting with N,N-dipropyl-2-(2-phthalimido-N-phenylacetamido)acetamide (2.7 g) and hydrazine hydrate (1.2 g). 2-(2-Amino-N-phenylacetamido)-N,N-dipropylacetamide (1.7 g) is thereby obtained in the form of an oil, which is used in the subsequent syntheses without further treatment.

N,N-dipropyl-2-(2-phthalimido-N-phenylacetamido)acetamide may be prepared in the following manner: oxalyl dichloride (1.7 g) and then one drop of dimethylformamide are added to a suspension of 2-(2-phthalimido-N-phenylacetamido)acetic acid (4 g) in 1,2-dichloroethane (50 cc). The mixture is stirred for 2 hours at a temperature in the region of 20° C. and dipropylamine (2.4 g), dissolved in 1,2-dichloroethane (20 cc), is then added. The solution obtained is stirred for 2 hours at a temperature in the region of 25° C., then washed with distilled water (2×30 cc), dried over magnesium sulphate and concentrated to dryness under reduced pressure (2.7 kPa) at 40° C. After recrystallization in diisopropyl ether, N,N-dipropyl-2-(2-phthalimido-N-phenylacetamido)acetamide (2.7 g), m.p. 130° C., is obtained.

2-(2-phthalimido-N-phenylacetamido)acetic acid may be prepared in the following manner: trifluoroacetic acid (17.9 g) is added to a solution of tert-butyl 2-(2-phthalimido-N-phenylacetamido)acetate (8 g) in dichloromethane (30 cc). The solution obtained is stirred under reflux for 1 hour and then concentrated to dryness under reduced pressure (2.7 kPa) at 40° C. After recrystallization in diisopropyl ether, 2-(2-phthalimido-N-phenylacetamido)acetic acid (5.9 g), m.p. 224° C., is obtained.

tert-Butyl 2-(2-phthalimido-N-phenylacetamido)acetate may be prepared in the following manner: sodium hydrogen carbonate (92.4 g) is added to a solution of tert-butyl N-phenylglycinate (207 g) in 1,2-dichloroethane (500 cc). The suspension is stirred at a temperature in the region of 5° C. and a solution of 2-phthalimidoacetyl chloride (223 g) in 1,2-dichloroethane (1100 cc) is added. The reaction mixture is stirred under reflux for 4 hours. After separation of the insoluble product by filtration, the filtrate is washed with distilled water (300 cc), dried over magnesium sulphate and concentrated to dryness under reduced pressure (2.7 kPa) at 40° C. After recrystallization in acetonitrile, tert-butyl 2-(2-phthalimido-N-phenylacetamido)acetate (236 g), m.p. 128° C., is obtained.

tert-Butyl N-phenyl glycinate may be prepared in the following manner: tert-butyl bromoacetate (58 g) is added to a solution of aniline (56 g) in 1,2-dichloroethane (600 cc), and the solution obtained is stirred under reflux for 48 hours. After cooling, the insoluble product is separated by filtration and the filtrate is washed with 0.1N aqueous hydrochloric acid solution (200 cc) and with distilled water (3×200 cc). The organic phase is dried over magnesium sulphate and then concentrated to dryness under reduced pressure (2.7 kPa) at 40° C. tert-Butyl N-phenyl glycinate (54 g) is thereby obtained in the form of an oil, which is used in the subsequent syntheses without further treatment.

2-Phthalimidoacetyl chloride may be prepared according to the method described by W. GRASSMANN and E. SCHULTE-UEBLING, Chem. Ber. 83, 244, (1950).

EXAMPLE 23

A solution of tert-butyl 2-(2-amino-N-phenylacetamido)acetate (2.64 g) in anhydrous 1,2-dichloroethane (25 cc) is added to a solution of N,N'-carbonyldiimidazole (1.78 g) in anhydrous 1,2 -dichloroethane (50 cc). The solution obtained is stirred for 1 hour at a temperature in the region of 20° C., 3-methylthioaniline (1.4 g) is then added and the mixture is heated to reflux for 4 hours. After cooling, dichloromethane (100 cc) is added and the reaction mixture is washed with water (3×75 cc), 0.1 N aqueous hydrochloric acid solution (3×75 cc) and then water (3×75 cc). The organic phase is dried over magnesium sulphate and concentrated to dryness under reduced pressure (2.7 kPa). The residue obtained is purified by chromatography on silica gel (0.04–0.063 mm; 250 g) contained in a column 3 cm in diameter [eluant: dichloromethane/methanol (97.5:2.5 by volume)], using an excess pressure of 40 kPa of nitrogen and collecting 20-cc fractions. Fractions 8 to 14 are combined and concentrated to dryness under reduced pressure (2.7 kPa) at 40° C. and the residue obtained is recrystallized in acetonitrile. tert-Butyl N-{2-[3-(3-methylthiophenyl)ureido]acetyl}-N-phenylglycinate (1.6 g), m.p. 139° C., is thereby obtained.

EXAMPLE 24

The procedure is similar to that described in Example 23, but starting with N,N'-carbonyldiimidazole (0.9 g) in anhydrous 1,2-dichloroethane (25 cc), tert-butyl 2-(2-amino-N-phenylacetamido)acetate (1.35 g) in anhydrous 1,2-dichloroethane (10 cc) and 3-methoxyaniline (0.62 g). After recrystallization in acetonitrile, tert-butyl N-{2-[3-(3-methoxyphenyl)ureido] acetyl}-N-[phenylglycinate (0.7 g), m.p. 136° C., is obtained.

EXAMPLE 25

Triethylamine (0.7 g), and then 2-indolecarbonyl chloride (1.2 g) dissolved in 1,2-dichloroethane (35 cc), are added to a solution, stirred at a temperature in the region of 25° C., of tert-butyl 2-(2-amino-N-phenylacetamido)acetate (1.2 g) in 1,2-dichloroethane (35 cc). The reaction mixture is stirred for 18 hours at a temperature in the region of 25° C. Dichloromethane (250 cc) is then added, followed by saturated aqueous sodium hydrogen carbonate solution (125 cc). The organic phase is washed with distilled water (2×125 cc), dried over magnesium sulphate and concentrated to dryness under reduced pressure (2.7 kPa) at 40° C. After recrystallization in acetonitrile, N-[N-(tert-butoxycarbonylmethyl) phenylcarbamoylmethyl]-2-indolecarboxamide (1 g), m.p. 203° C., is obtained.

2-Indolecarbonyl chloride may be prepared in the following manner: dimethylformamide (0.1 cc), and then oxalyl dichloride (1.5 g) dissolved in anhydrous diethyl ether (10 cc), are added to a suspension of 2-indolecarboxylic acid (1.85 g) in anhydrous diethyl ether (40 cc) at a temperature in the region of 5° C. The reaction mixture is stirred at a temperature in the region of 25° C. for 2 hours. The ether phase is concentrated to dryness under reduced pressure (2.7 kPa) at 30° C. 2-Indolecarbonyl chloride (1.8 g), m.p. 120° C., is thereby obtained.

EXAMPLE 26

4-Dimethylaminopyridine (5 mg) and then N,N'-carbonyldiimidazole (1.78 g) are added to a solution of 3,4-dichlorobenzoic acid (1.91 g) in anhydrous 1,2-dichloroethane (50 cc). The solution obtained is stirred for 2 hours at a temperature in the region of 20° C., tert-butyl 2-(2-amino-N-phenylacetamido)acetate (2.64 g) is then added and the mixture is stirred for 3 hours at a temperature in the region of 20° C. The reaction mixture is then washed with water (3×75 cc), and the organic phase is separated, dried over magnesium sulphate and concentrated to dryness under reduced pressure (2.7 kPa). The residue obtained is purified by chromatography on silica gel (0.04–0.063 mm; 250 g) contained in column 4.2 cm in diameter [eluant: dichloromethane/methanol (98:2 by volume)], using an excess pressure of 40 kPa of nitrogen and collecting 20-cc fractions. Fractions 7 to 15 are combined and concentrated to dryness under reduced pressure (2.7 kPa) at 40° C. and the residue is recrystallized in a mixture of cyclohexane and 2-propanol (80:20 by volume). tert-Butyl N-[N- (3,4-dichlorobenzoyl)glycyl]-N-phenylglycinate (1.5 g), m.p. 95° C., is thereby obtained.

EXAMPLE 27

The procedure is similar to that described in Example 26, but starting with 2-naphthoic acid (1.72 g), 4-dimethylaminopyridine (5 mg), N,N'-carbonyldiimidazole (1.78 g) and tert-butyl 2-(2-amino-N-phenylacetamido- )acetate (2.64 g). After recrystallization in a mixture of heptane and 2-propanol (70:30 by volume), tert-butyl N-[N-(2-naphthoyl)glycl]-N-phenylglycinate (2.3 g), m.p. 108° C., is thereby obtained.

EXAMPLE 28

A suspension of cyclopropyl 2-anilinoacetate (2.9 g) and 2-[3-(3-methylphenyl)ureido]acetic acid in anhydrous 1,2-dichloroethane (50 cc) is heated to reflux. Thionyl chloride (1.0 cc) is then added, refluxing being maintained until the gaseous evolution has ceased. The reaction mixture is then poured into saturated aqueous sodium hydrogen carbonate solution (30 cc) and thereafter methylene chloride (50 cc) is added. The organic phase is washed with distilled water (50 cc), dried over magnesium sulphate and concentrated to dryness under reduced pressure (2.7 kPa) at 40° C. After recrystallization in acetonitrile, cyclopropylmethyl 2-{2-[3-(3-methylphenyl)ureido]-N-phenylacetamido}acetate (1.6 g), m.p. 158° C., is obtained.

Cyclopropylmethyl 2-anilinoacetate may be prepared in the following manner: cyclopropylmethyl bromoacetate (4 g) is added to a solution of aniline (3.7 g) in acetonitrile (50 cc), and the mixture is stirred under reflux for 3 hours. The insoluble product is separated by filtration and the filtrate is concentrated to dryness under reduced pressure (2.7 kPa) at 40° C. The product obtained is purified by chromatography on silica gel (0.065-0.200 mm; 50 g) contained in a column 2 cm in diameter [eluant: cyclohexane/ethyl acetate (70:30 by volume)], collecting 20-cc fractions. Fractions 3 to 5 are combined and concentrated to dryness under reduced pressure (2.7 kPa) at 40° C. Cyclopropylmethyl 2-anilinoacetate (2.9 g) is thereby obtained in the form of an oil, which is used in the subsequent syntheses without further treatment.

Cyclopropylmethyl bromoacetate may be prepared in the following manner: bromoacetyl bromide (6 g) is added in the course of 20 minutes to a solution, maintained at a temperature in the region of 5° C., of cyclopropylmethanol (2.3 g) and triethylamine (3.3 g) in diethyl ether (40 cc), and the mixture is then stirred for 2 hours at a temperature in the region of 25° C. The insoluble product is separated by filtration and the filtrate is washed successively with 4N aqueous hydrochloric acid solution (20 cc), saturated aqueous sodium hydrogen carbonate solution (20 cc) and distilled water (25 cc), then dried over magnesium sulphate and concentrated to dryness under reduced pressure (2.7 kPa) at 30° C. Cyclopropylmethyl bromoacetate (4 g) is thereby obtained in the form of an oil, which is used in the subsequent syntheses without further treatment.

2-[3-(3-Methylphenyl)ureido]acetic acid may be prepared in the following manner: 3-methylphenyl isocyanate (53 g) is added in the course of 15 minutes to a solution of glycine (30 g) and sodium hydrogen carbonate (53 g) in distilled water (600 cc). The reaction mixture is stirred for 4 hours at a temperature in the region of 25° C., then washed with ethyl acetate (200 cc) and acidified to pH 1 with 4N hydrochloric acid solution (200 cc). The product obtained is separated by filtration, washed with water and dried in the air. 2-[3-(3-Methylphenyl) ureido]acetic acid (72 g), m.p. 208° C., is thereby obtained.

EXAMPLE 29

The procedure is similar to that described in Example 28, but starting with tert-butyl (RS)-2-anilino-2-phenylacetate (1.5 g), 2-[3-(3-methylphenyl)ureido]acetic acid (1.1 g) and thionyl chloride (0.63 g). The product obtained is purified by chromatography on silica gel (0.063-0.200 mm; 30 g) contained in a column 2.2 cm in diameter [eluant: methylene chloride/ethyl acetate (97:3 by volume)], collecting 20-cc fractions. Fractions 12 to 35 are combined and concentrated to dryness under reduced pressure (2.7 kPa) at 40° C. After recrystallization in a mixture of diisopropyl ether and hexane (65:35 by volume), tert-butyl (RS)-2-{2-[3-(3-methylphenyl)ureido]-N-phenylacetamido}phenylacetate (0.85 g), m.p. 131° C., is obtained.

tert-Butyl (RS)-2-anilino-2-phenylacetate may be prepared in a manner similar to that described in Example 28 for the preparation of cyclopropylmethyl 2-anilinoacetate, but starting with tert-butyl α-bromophenylacetate (6.7 g) and aniline (3.7 g). The product obtained is purified by chromatography on silica gel (0.063-0.200 mm; 25 g) contained in a column 2.7 cm in diameter [eluant: petroleum ether/ethyl acetate (85:15 by volume)], collecting 20-cc fractions. Fractions 6 to 10 are combined and concentrated to dryness under reduced by pressure (2.7 kPa) at 40° C. tert-Butyl (RS)-2-anilino-2-phenylacetate (1.6 g), m.p. 94° C., is thereby obtained.

tert-Butyl α-bromophenylacetate may be prepared in a manner similar to that described in Example 28 for the preparation of cyclopropylmethyl bromoacetate, but starting with 2-methyl-2-propanol (21.8 g), N,N-dimethylaniline (replacing triethylamine; 21.4 g) and α-bromophenylacetyl chloride (16 g). tert-Butyl α-bromophenylacetate (8.1 g) is thereby obtained in the form of a yellow oil.

α-Bromophenylacetyl chloride may be prepared according to the method described by V. L. NARAYANAN and C. F. MARTIN, J. Med. Chem., 9, 616 (1966).

EXAMPLE 30

The procedure is similar to that described in Example 28, but starting with (RS)-sec-butyl 2-anilinoacetate (1.8 g), 2-[3-(3-methylphenyl)ureido]acetic acid (1.8 g) and thionyl chloride (0.6 cc). The oily residue obtained is purified by chromatography on silica gel (0.063-0.200 mm; 30 g) contained in a column 1.5 cm in diameter [eluant: dichloromethane/methanol (70:30 by volume)], collecting 20-cc fractions. Fractions 10 to 12 are combined and concentrated to dryness under reduced pressure (2.7 kPa) at 40° C. After recrystallization in isopropyl ether, (RS)-sec-butyl 2-({2-[3-(3-methylphenyl)ureido]-N-phenylacetamido}acetate (0.7 g), m.p. 136° C., is obtained.

(RS)-sec-Butyl 2-anilinoacetate may be prepared in a manner similar to that described in Example 28 for the preparation of cyclopropylmethyl 2-anilinoacetate, but starting with (RS)-sec-butyl bromoacetate (2.7 g) and aniline (2.7 g). The product obtained is purified by chromatography on silica gel (0.063-0.200 mm; 50 g) contained in a column 2 cm in diameter [eluant: cyclohexane/ethyl acetate (70:30 by volume)], collecting 20-cc fractions. Fractions 2 to 5 are combined and concentrated to dryness under reduced pressure (2.7 kPa) at 40° C. (RS)-sec-butyl 2-anilinoacetate (1.8 g) is thereby obtained in the form of an oil, which is used in the subsequent syntheses without further treatment.

(RS)-sec-Butyl bromoacetate may be prepared in a manner similar to that described in Example 28 for the preparation of cyclopropylmethyl bromoacetate, but starting with (RS)-2-butanol (2.2 g), triethylamine (3.2 g) and bromoacetyl bromide (6 g). (RS)-sec-Butyl bromoacetate (2.7 g) is thereby obtained in the form of an oil, which is used in the subseqent syntheses without further treatment.

EXAMPLE 31

Working in a manner similar to that described in Example 28, but starting with ethyl 2-anilinoacetate (2.2 g), 2-[3-(3-methylphenyl)ureido]acetic acid (2.6 g) and thionyl chloride (1.50 g), and after recrystallization in isopropanol, ethyl 2-{2-[3-(3-methylphenyl)ureido]-N-phenylacetamido}acetate (2 g), m.p. 181° C., is obtained.

Ethyl 2-anilinoacetate may be prepared in a manner similar to that described in Example 28 for the preparation of cyclopropylmethyl 2-anilinoacetate, but starting with aniline (10.8 g) and ethyl bromoacetate (9.3 g). Ethyl 2-anilinoacetate (7 g), m.p. approximately 40° C., is thereby obtained.

EXAMPLE 32

The procedure is similar to that described in Example 28, but starting with benzyl 2-anilinoacetate (3.6 g), 2-[3-(3-methylphenyl)ureido]acetic acid (3.1 g) and thionyl chloride (1.65 g). The product obtained is purified by chromatography on silica gel (0.063–0.200 mm; 60 g) contained in a column 2 cm in diameter [eluant: cyclohexane/ethyl acetate (50:50 by volume)], collecting 20-cc fractions. Fractions 5 to 9 are combined and concentrated to dryness under reduced pressure (2.7 kPa) at 40° C. After recrystallization in acetonitrile, benzyl 2-{2-[3-(3-methylphenyl)ureido]-N-phenylacetamido}acetate (1.4 g), m.p. 140° C., is obtained.

Benzyl 2-anilinoacetate may be prepared in a manner similar to that described in Example 28 for the preparation of cyclopropylmethyl 2-anilinoacetate, but starting with aniline (3.9 g) and benzyl bromoacetate (4.9 g). The product obtained is purified by chromatography on silica gel (0.063–0.200 mm; 50 g) contained in a column 1.5 cm in diameter [eluant: cyclohexane/ethyl acetate (70:30 by volume)], collecting 20-cc fractions. Fractions 3 to 6 are combined and concentrated to dryness under reduced pressure (2.7 kPa) at 40° C. Benzyl 2-anilinoacetate (3.8 g) is obtained in the form of an oil, which is used in the subsequent syntheses without further treatment.

Benzyl bromoacetate may be prepared in a manner similar to that described in Example 28 for the preparation of cyclopropylmethyl bromoacetate, but starting with benzyl alcohol (2.7 g), triethylamine (2.8 g) and bromoacetyl bromide (5 g). Benzyl bromoacetate (4.9 g) is thereby obtained in the form of an oil, which is used in the subsequent syntheses without further treatment.

EXAMPLE 33

The procedure is similar to that described in Example 28, but starting with cyclohexyl 2-anilinoacetate (8.6 g), 2-[3-(3-methylphenyl)ureido]acetic acid (7.7 g) and thionyl chloride (2.7 cc). The product obtained is purified by chromatography on silica gel (0.063–0.200 mm; 150 g) contained in a column 3.5 cm in diameter [eluant: methylene chloride/methanol (99:1 by volume)], collecting 20-cc fractions. Fractions 6 to 18 are combined and concentrated to dryness under reduced pressure (2.7 kPa) at 40° C. After recrystallization in isopropanol, cyclohexyl 2-{2-[3-(3-methylphenyl)ureido]-N-phenylacetamido}acetate (2.3 g), m.p. 176° C., is obtained.

Cyclohexyl 2-anilinoacetate may be prepared in a manner similar to that described in Example 28 for the preparation of cyclopropylmethyl 2-anilinoacetate, but starting with cyclohexyl bromoacetate (11.5 g) and aniline (9.7 g). The product obtained is purified by chromatography on silica gel (0.063–0.200 mm; 180 g) contained in a column 3.5 cm in diameter [eluant: cyclohexane/ethyl acetate (70:30 by volume)], collecting 20-cc fractions. Fractions 2 to 10 are combined and concentrated to dryness under reduced pressure (2.7 kPa) at 40° C. Cyclohexyl 2-anilinoacetate (8.6 g), m.p. approximately 50° C., is thereby obtained.

Cyclohexyl bromoacetate may be prepared in a manner similar to that described in Example 28 for the preparation of cyclopropylmethyl bromoacetate, but starting with cyclohexanol (9 g), triethylamine (9.9 g) and bromoacetyl bromide (18 g). The product obtained is purified by chromatography on silica gel (0.063–0.200 mm; 200 g) contained in a column 3.5 cm in diameter [eluant: cyclohexane/ethyl acetate (80:20 by volume)], collecting 20-cc fractions. Fractions 3 to 12 are combined and concentrated to dryness under reduced pressure (2.7 kPa) at 40° C. Cyclohexyl bromoacetate (11.5 g) is thereby obtained in the form of an oil, which is used in the subsequent syntheses without further treatment.

EXAMPLE 34

Phenyl 2-{2-[3-(3-methylphenyl)ureido]-N-phenylacetamido}acetate may be prepared in the following manner: triethylamine (0.6 g) and 1-benzotriazolyloxytris(dimethylamino)phosphonium hexafluorophosphonate (1.28 g) are added to a suspension of 2-{2-[3-(3-methylphenyl)ureido]-N-phenylacetamido}acetic acid (1 g) and phenol (0.28 g) in methylene chloride (60 cc). The solution obtained is stirred for 2 hours at a temperature in the region of 25° C. and then poured into saturated aqueous sodium chloride solution (50 cc). The organic phase is separated and the aqueous phase is extracted with ethyl acetate (3×80 cc). The combined organic phases are washed successively with 2N aqueous hydrochloric acid solution (2×30 cc), saturated aqueous sodium hydrogen carbonate solution (2×30 cc) and saturated aqueous sodium chloride solution (50 cc), dried over magnesium sulphate and concentrated to dryness under reduced pressure (2.7 kPa) at 40° C. After recrystallization in acetonitrile, phenyl 2-{2-[3-(3-methylphenyl)ureido]-N-phenylacetamido}acetate (0.7 g), m.p. 206° C., is obtained.

2-{2-[3-(3-Methylphenyl)ureido]-N-phenylacetamido}acetic acid may be prepared in the following manner: trifluoroacetic acid (7 g) is added to a solution of tert-butyl 2-{2-[3-(3-methylphenyl)ureido]-N-phenylacetamido}acetate (3.3 g) in dichloromethane (25 cc). The solution obtained is stirred under reflux for 4 hours and then concentrated to dryness under reduced pressure (2.7 kPa) at 40° C.

After recrystallization in diisopropyl ether, 2-{2-[3-(3-methylphenyl)ureido]-N-phenylacetamido}acetic acid (2 g), m.p. 188° C., is obtained.

EXAMPLE 35

A suspension of (RS)-N-(3-methylphenylcarbamoyl)-phenylglycine (5 g) and tert-butyl anilinoacetate (3.6 g) in anhydrous 1,2-dichloroethane (300 cc) is heated to reflux while stirring. Thionyl chloride (1.3 cc) is then added, refluxing being maintained for 10 minutes. After cooling, the reaction mixture is poured into saturated aqueous sodium bicarbonate solution (100 cc), and the organic phase is washed with water (100 cc), dried over magnesium sulphate and concentrated to dryness under reduced pressure (2.7 kPa) at 40° C. The residue obtained is purified by chromatography on silica gel (0.04-0.063 mm; 250 g) contained in a column 5 cm in diameter [eluant: dichloromethane/methanol (98:2 by volume)], using an excess pressure of 40 kPa of nitrogen and collecting 100-cc fractions. Fractions 16 to 21 are combined and concentrated to dryness under reduced pressure (2.7 kPa) at 40° C. and the residue obtained is recrystallized in diisopropyl ether. tert-Butyl (RS)-N-{2-[3-(3-methylphenyl)ureido]-2-phenylacetyl}-N-phenylglycinate (4.3 g), m.p. 178° C., is thereby obtained.

(RS)-N-(3-Methylphenylcarbamoyl)phenylglycine may be prepared in the following manner: 3-methylphenyl isocyanate (5.14 cc) is added in the course of 1 minute to a suspension of (RS)-phenylglycine (6.05 g) and sodium hydrogen carbonate (3.36 g) in water (100 cc). The mixture is stirred for 20 hours at a temperature in the region of 20° C. and is then extracted with ethyl acetate (3×75 cc). The organic phase is washed with water (2×50 cc) and the combined aqueous extracts are acidified to pH 1 with 4N aqueous hydrochloric acid solution. The precipitate obtained is separated by filtration, washed with water and dried under reduced pressure (0.07 kPa) at 40° C. (RS)-N-(3-Methylphenylcarbamoyl)phenylglycine (5 g), m.p. 198° C., is thereby obtained.

EXAMPLE 36

The procedure is as in Example 35, but starting with (RS)-N-(3-methylphenylcarbamoyl) phenylglycine (5.7 g), diphenylamine (3.38 g) in anhydrous 1,2-dichloroethane (350 cc) and thionyl chloride (1.45 cc). After recrystallization in diethyl ether, (RS)-2-[3-(3-methylphenyl)ureido]-2-phenyl-N,N-diphenylacetamide (2 g), m.p. 181° C. is obtained.

EXAMPLE 37

The procedure is as in Example 35, but starting with N-(3-methylphenylcarbamoyl)-β-alanine (4.8 g), tert-butyl anilinoacetate (4.5 g) and thionyl chloride (1.6 cc). After recrystallization in diethyl ether, tert-butyl (RS)-2-{3-[3-(3-methylphenyl)ureido]-N-phenylpropionamido}acetate (4.1 g), m.p. 142° C., is obtained.

N-(3-Methylphenylcarbamoyl)-β-alanine may be prepared in a manner similar to that described in Example 35 for the preparation of (RS)-N-(3-methylphenylcarbamoyl)phenylglycine, but starting with β-alanine (3.56 g), sodium hydrogen carbonate (3.36 g) and 3-methylphenyl isocyanate (5.14 cc). N-(3-Methylphenylcarbamoyl)-β-alanine (4.87 g), m.p. 166° C., is thereby obtained.

EXAMPLE 38

The procedure is as in Example 35, but starting with (RS)-N-(3-methylphenylcarbamoyl)valine (5 g), tert-butyl anilinoacetate (4.1 g) and thionyl chloride (1.45 cc). After 2 successive recrystallizations, first in diisopropyl ether and then in cyclohexane, tert-butyl (RS)-2-{2-[3-(3-methylphenyl)ureido]-3-methyl-N-phenylbutyramino}acetate (3.5 g), m.p. 154° C., is obtained.

(RS)-N-(3-Methylphenylcarbamo-yl)valine may be prepared in a manner similar to that described in Example 35 for the preparation of (RS)-N-(3-methylphenylcarbamoyl)phenylglycine, but starting with (RS)-valine (4.7 g), sodium hydrogen carbonate (3.36 g) and 3-methylphenyl isocyanate (5.14 cc). (RS)-N-(3-Methylphenylcarbamoyl)valine (6.6 g), m.p. 170° C., is thereby obtained.

The present invention also relates to medicinal products consisting of at least one compound of formula (I), in the pure state or in the form of a composition in which it is combined with any other pharmaceutically compatible product, which can be inert or physiologically active. The medicinal products according to the invention may be employed orally parenterally, rectally or topically.

As solid compositions for oral administration, tablets, pills, powders (gelatin capsules, wafer capsules) or granules may be used. In these compositions, the active principle according to the invention is mixed with one or more inert diluents such as starch, cellulose, sucrose, lactose or silica. These compositions can also comprise substances other than diluents, e.g. one or more lubricants such as magnesium stearate or talc, a coloring, a coating (dragées) or a varnish.

As liquid compositions for oral administration, solutions, suspensions, emulsions, syrups and elixirs of a pharmaceutically acceptable nature, containing inert diluents, such as water, ethanol, glycerol, vegetable oils or liquid paraffin, may be used. These compositions can comprise substances other than diluents, e.g. wetting products, sweeteners, thickeners, flavorings or stabilizers.

The sterile compositions for parenteral administration can preferably be aqueous solutions or non-aqueous solutions, suspensions or emulsions. As a solvent or vehicle, water, propylene glycol, a polyethylene glycol, vegetable oils, especially olive oil, injectable organic esters, e.g. ethyl oleate, or other suitable organic solvents may be employed. These compositions can also contain adjuvants, especially wetting agents, tonicity regulators, emulsifiers, dispersants and stabilizers. The sterilization may be carried out in several ways, e.g. by aseptic filtration, by incorporating sterilizing agents in the composition, by irradiation or by heating. They may also be prepared in the form of sterile solid compositions which can be dissolved at the time of use in a sterile injectable medium.

The compositions for rectal administration are suppositories or rectal capsules which contain, apart from the active product, excipients such as coco butter, semisynthetic glycerides or polyethylene glycols.

The compositions for topical administration can be, e.g. creams, ointments, lotions, eye washes, mouth washes, nasal drops or aerosols.

In human therapy, the compounds according to the invention are especially useful in the treatment and prevention of disorders linked to CCK in respect of the nervous system and the gastrointestinal apparatus. These compounds may hence be used in the treatment and prevention of psychoses, the anxiety disorders of Parkinson's disease, tardive dyskinesia, irritable colon syndrome, acute pancreatitis, ulcers, disorders of intestinal motility and some tumors of the lower oesophagus, colon and intestine, as a potentiator of the activity of narcotic and non-narcotic analgesic medicinal products and as an appetite regulator.

The doses depend on the effect sought, the treatment period and the administration route used; they are generally between 0.05 g and 1 g per day in oral administration for an adult, with unit doses ranging from 10 mg to 500 mg of active substance.

Generally speaking, the doctor will determine the appropriate dosage in accordance with the age and weight and all other factors characteristic of the subject to be treated.

The examples which follow illustrate compositions according to the invention:

EXAMPLE A

Hard gelatin capsules containing 50 mg of active product and having the following composition are prepared according to the usual technique:

| | |
|---|---|
| N,N-Diphenyl-2-[3-(3-ethylphenyl)ureido]-acetamide | 50 mg |
| Cellulose | 18 mg |
| Lactose | 55 mg |
| Colloidal silica | 1 mg |
| Carboxymethylstarch sodium | 10 mg |
| Talc | 10 mg |
| Magnesium stearate | 1 mg |

EXAMPLE B

Tablets containing 50 mg of active product and having the following composition are prepared according to the usual technique:

| | |
|---|---|
| N,N-Diphenyl-2-(3-phenylureido)acetamide | 50 mg |
| Lactose | 104 mg |
| Cellulose | 40 mg |
| Polyvidone | 10 mg |
| Carboxymethylstarch sodium | 22 mg |
| Talc | 10 mg |
| Magnesium stearate | 2 mg |
| Colloidal silica | 2 mg |
| Mixture of hydroxymethylcellulose, glycerol and titanium oxide (72:3.5:24.5) | q.s. 1 finished film-coated tablet weighing 245 mg |

EXAMPLE C

An injectable solution containing 10 mg of active product and having the following composition is prepared:

| | |
|---|---|
| tert-Butyl 2-{2-[3-(3-methylphenyl)ureido]-N-phenylacetamido}acetate | 10 mg |
| Benzoic acid | 80 mg |
| Benzyl alcohol | 0.06 cc |
| Sodium benzoate | 80 mg |
| Ethanol, 95% | 0.4 cc |
| Sodium hydroxide | 24 mg |
| Propylene glycol | 1.6 cc |
| Water q.s. | 4 cc |

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:

1. A compound of formula:

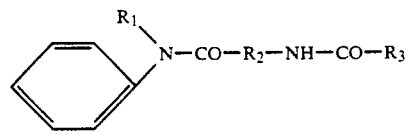

in which
R$_1$ represents:
  a phenyl radical or phenyl radical substituted with an alkyl, alkoxy or cyano radical or with a halogen atom,
  a chain —CH(R$_8$)—COOR$_4$ in which R$_4$ represents a hydrogen atom or an alkyl, cycloalkyl, cycloalkylalkyl, phenylalkyl or phenyl radical and R$_8$ represents a hydrogen atom or an alkyl or phenyl radical,
  a chain —CH$_2$—CO—NR$_5$R$_6$ in which R$_5$ and R$_6$, which may be identical or different, represent an alkyl radical or, with the nitrogen atom to which they are attached, form a 1-pyrrolidinyl radical optionally substituted with an alkyl radical, or
  a phenylalkyl radical,
R$_2$ represents a methylene or ethylene radical or a radical —CH(R$_7$)— in which R$_7$ represents an alkyl radical, phenyl radical or benzyl radical, alkylthioalkyl radical in which the alkyl portions contain 1 or 2 carbon atoms
R$_3$ represents a 1- or 2-naphthyl radical, 2- or 3-indolyl radical or phenylamino radical in which the phenyl ring is optionally substituted with an alkyl, alkoxy, nitro, hydroxyl or alkylthio radical or with 1 or 2 halogen atoms, on the understanding that, when R$_3$ represents a 1- or 2-naphthyl or 2- or 3-indolyl radical, R$_7$ cannot represent a benzyl or alkylthioalkyl or phenyl radical, and that, except where otherwise stated, the alkyl and alkoxy radicals and alkyl and alkoxy portions contain 1 to 4 carbon atoms in a straight or branched chain, as well as, when R$_2$ represents a radical —CH(R$_7$)—, its racemates and its stereoisomers.

2. The compound of formula (I) according to claim 1 for which
R$_1$ represents
  a phenyl radical optionally substituted with an alkoxy radical or with an a halogen atom, or
  a chain —CH(R$_8$)—COOR$_4$ in which R$_4$ represents an alkyl or cycloalkylalkyl radical and R$_8$ represents a hydrogen atom or a phenyl radical, and
R$_2$ and R$_3$ have the same meanings as in claim 1.

3. A medicinal product which contains, as active principle, at least one compound of formula (I) according to claim 1, in the pure state or in the form of a combination with one or more compatible and pharmaceutically acceptable diluents or adjuvants.

4. The medicinal product according to claim 3, for the treatment or prevention of disorders linked to CCK in respect of the nervous system and the gastrointestinal apparatus.

* * * * *